United States Patent [19]

Bicking et al.

[11] 4,112,236
[45] Sep. 5, 1978

[54] INTERPHENYLENE 8-AZA-9-DIOXOTHIA-11,12-SECOPROSTA-GLANDINS

[75] Inventors: John B. Bicking; Edward J. Cragoe, Jr., both of Lansdale, Pa.

[73] Assignee: Merck & Co., Inc., Rahway, N.J.

[21] Appl. No.: 783,998

[22] Filed: Apr. 4, 1977

[51] Int. Cl.$^2$ .................. C07C 143/75; A61K 31/21; A61K 31/19
[52] U.S. Cl. .................................... 560/12; 562/430; 424/309; 424/319
[58] Field of Search ...................... 560/12 (U.S. only); 260/470, 519

[56] References Cited

U.S. PATENT DOCUMENTS 3,991,106  11/1976  Cragoe ............................. 260/516

FOREIGN PATENT DOCUMENTS 1,429,092  3/1976  United Kingdom.

Primary Examiner—James O. Thomas, Jr.
Assistant Examiner—Michael Shippen

Attorney, Agent, or Firm—Thomas E. Arther; Harry E. Westlake, Jr.; Rudolph J. Anderson, Jr.

[57] ABSTRACT

Interphenylene 8-aza-9-dioxothia-11,12-secoprostaglandins are prepared by the two-stage alkylation of the anion of a lower alkyl sulfonamide, $R^1SO_2NH_2$, using first a compound of the formula:

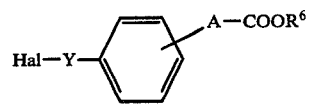

and second, a compound of the formula:

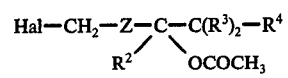

The compounds produced have renal vasodilatory activity when administered orally and are therefore useful for treating patients with renal impairment.

28 Claims, No Drawings

INTERPHENYLENE 8-AZA-9-DIOXOTHIA-11,12-SECOPROSTAGLANDINS

SUMMARY OF THE INVENTION

This invention relates to novel interphenylene 8-aza-9-dioxothia-11,12-secoprostaglandin compounds which can be represented by the following formula:

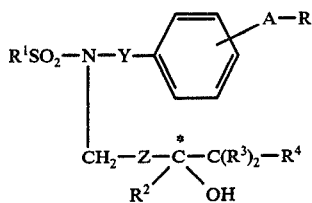

wherein R is selected from the group consisting of carboxy and a carboxy salt which incorporates a pharmaceutically acceptable cation such as metal cations derived from alkali metals, alkaline earth metals, and amines such as ammonia, primary and secondary amines, and quaternary ammonium hydroxides. Especially preferred metal cations are those derived from alkali metals, e.g., sodium, potassium, and lithium.

R is also selected from alkoxycarbonyl (—COOR$^5$) wherein R$^5$ is alkyl having 1–10 carbon atoms.

A is selected from a group consisting of $(CH_2)_n$ wherein n is 0 (a single bond) or 2 or oxymethylene (—O—CH$_2$—) or vinylene (—CH=CH—).

Y is selected from the group consisting of $(CH_2)_n$ where n is 1, 3, or 4.

The groups Y and —A—R can be located ortho, meta, or para to each other on the benzene ring, and the sum of chain-forming elements (C and O) in A and Y is limited to either 3 or 4.

Z is selected from the group consisting of ethylene (—CH$_2$—CH$_2$—), vinylene (—CH=CH—), and ethynylene (—C≡C—).

R$^1$ is lower alkyl of 1–4 carbon atoms.

R$^2$ is independently selected from the group consisting of hydrogen and methyl.

R$^3$ is independently selected from the group consisting of hydrogen and methyl.

R$^4$ is lower alkyl of 3–6 carbon atoms, either straight or branched (e.g., propyl, butyl, amyl, isoamyl, hexyl, 3,3-dimethylbutyl), or 3-butenyl.

In addition, when R$^4$ is lower alkyl and R$^2$ is methyl, they can be joined together (with abstraction of two hydrogen atoms) to form a carbocyclic ring with from 6 to 9 members.

Also, when R$^4$ is lower alkyl and R$^2$ is hydrogen, R$^4$ can be joined to the carbon atom bearing R$^2$ and OH to form a carbocyclic ring with from 5 to 8 members.

It is to be recognized that the carbon atom marked by an asterisk (*) and, in addition, certain carbon atoms included in R$^4$, chiral. The compounds of this invention are understood to include the individual stereoisomers and mixtures of stereoisomers, the biological activity of which will vary but which may readily be determined in the in vitro and in vivo assays described herein.

BACKGROUND OF THE INVENTION

The compounds of formula I are interphenylene 8-aza-9-dioxothia-11,12-secoprostaglandins because of a formal resemblance between structural features of these compounds and the natural prostaglandins.

The prostaglandins constitute a class of highly functionalized C$_{20}$ fatty acids. They have been shown to occur extensively in low concentrations in mammalian tissues where they are both rapidly anabolized and catabolized and to exhibit a broad spectrum of pharmacological activities including prominent roles is (a) functional hyperemia, (b) the inflammatory response, (c) the central nervous system, (d) transport of water and electrolytes, and (e) regulation of cyclic AMP. Further details concerning the prostaglandins can be found in recent reviews of their chemistry, [J. E. Pike, FORTSCHR. CHEM. ORG. NATURST., 28, 313 (1970) and G. F. Bundy, A. REP. IN MED. CHEM., 7, 157 (1972)]; biochemistry [J. W. Hinman, A. REV. BIOCHEM., 41, 161 (1972)]; pharmacology [J. R. Weeks, A. REV. PHARM., 12, 317 (1972)]; physiological significance [E. W. Horton, PHYSIOL. REV., 49, 122 (1969)]; and general clinical application [J. W. Hinman, POSTGRAD. MED. J., 46, 562 (1970)].

The potential application of natural prostaglandins as medicinally useful therapeutic agents in various mammalian disease states is obvious but suffers from three formidable major disadvantages, namely, (a) prostaglandins are known to be rapidly metabolized in vivo in various mammalian tissues to a variety of metabolites which are devoid of the desired original biological activities, (b) the natural prostaglandins are inherently devoid of biological specificity which is requisite for a successful drug, and (c) although limited quantitites of prostaglandins are presently produced by both chemical and biochemical processes, their production cost is extremely high; and consequently, their availability is quite restricted.

Out interest has, therefore, been to synthesize novel compounds structurally related to the natural prostaglandins, but with the following unique advantages; (a) simplicity of synthesis leading to low cost of production; (b) specificity of biological activity; and (c) enhanced metabolic stability so that activity can be obtained on oral as well as parenteral administration.

These advantages have been realized in the compounds of this invention. Certain of the compounds exhibit renal vasodilatory activity on oral administration and, therefore, are useful for the treatment of patients with renal impairment. Included in this group are patients with hypertension, renal failure, congestive heart failure, glomerulonephritis, uremia, and chronic renal insufficiency. The compounds of this invention by virtue of their renal vasodilatory activity improve renal function both when used alone or in conjunction with other renal agents. An example of a compound with renal vasodilotory activity is 4-{3-[N-(3-(1-hydroxycyclohexyl)propyl)methanesulfonamido]-propyl}benzoic acid.

In addition to their activity as renal vasodilators, many compounds of this invention have useful adjunctive properties which give them added utility for the treatment of renal disease. Such properties include diuretic, saluretic, antihypertensive, and immunoregulant activities.

With regard to the indications that the compounds of this invention can be useful in therapy as regulators of the immune response, it can be stated that the basis for their activity in this area is their ability to stimulate cyclic-AMP formation in cells. Agents, including the E prostaglandins, that increase cellular cyclic-AMP concentration, interfere with the cell-mediated immune response by inhibiting lymphocyte expression in response to antigen, by inhibiting release of pathological mediators from sensitized lymphocytes, and by inhibiting the killing of target cells by such lymphocytes. Various assays which depend upon the measurement of some function of the immunologically competent lymphocyte can be used to demonstrate that the prostaglandin analogs of this invention are similarly active. For example, the release of lymphokines (proteins that are agents of inflammation and tissue destruction) from sensitized lymphocytes in culture is strongly inhibited by these analogs in low concentrations. Thus, it is apparent that the compounds of this invention are applicable to the treatment of those autoimmune diseases in whose pathogenesis a cell-mediated immune reaction is involved. Such diseases range from contact dermatitis to such chronic destructive diseases as rheumatoid arthritis and possibly multiple sclerosis and systemic lupus erythematosus.

Since the rejection of organ grafts is considered to be predominantly a cell-mediated immune phenomenon, a further area of usefulness of the compounds of this invention is in the prevention of transplant rejection.

The compounds of this invention can be administered intravenously, subcutaneously, intramuscularly, orally, rectally, or by aerosolization in the form of sterile implants for long action. They can be formulated in any of a number of pharmaceutical compositions and non-toxic carriers to this end.

The pharmaceutical compositions can be sterile, injectable suspensions or solutions, or solid orally administrable, pharmaceutically acceptable tablets or capsules; the compositions can also be intended for sublingual administration, or for suppository use. It is especially advantageous to formulate compositions in dosage unit forms for ease and economy of administration and uniformity of dosage. "Dosage unit form" as a term used herein refers to physically discrete units suitable as unitary dosages for animal and human subjects, each unit containing a predetermined quantity of active material calculated to produce the desired biological effect in association with the required pharmaceutical means.

Illustratively, a sterile injectable composition can be in the form of aqueous or oleagenous suspensions or solutions.

The sterile injectable composition can be aqueous or oleagenous suspension or solution. Suspensions can be formulated according to the known art using suitable dispersing and wetting agents and suspending agents. Solutions are similarly prepared from the salt form of the compound. For the laboratory animals, we prefer to use incomplete Freund's adjuvant or sterile saline (9%) as carrier. For human parenteral use, such as intramuscularly, intravenously, or by regional perfusion, the diluent can be a sterile aqueous vehicle containing a preservative; for example, methylparaben, propylparaben, phenol, and chlorobutanol. The aqueous vehicle can also contain sodium chloride, preferably in an amount to be isotonic; as well as a suspending agent, for example, gum arabic, polyvinyl pyrrolidone, methyl cellulose, acetylated monoglyceride (available commercially as Myvacet from Distillation Products Industry, a division of Eastman Kodak Company), monomethyl, glyceride, dimethyl glyceride, or a moderately high molecular weight polysorbitan (commercially available under the tradenames Tween or Span from Atlas Powder Company, Wilmington, Delaware). Other materials employed in the preparation of chemotherapeutic compositions containing the compound may include glutathione, 1,2-propanediol, glycerol, and glucose. Additionally, the pH of the composition is adjusted by use of an aqueous solution such as tris(hydroxymethyl)aminomethane (tris buffer).

Oily pharmaceutical carriers can also be used, since they dissolve the compound and permit high doses. Many oily carriers are commonly employed in pharamceutical use, such as, for example, mineral oil, lard, cottonseed oil, peanut oil, sesame oil, or the like.

It is preferred to prepare the compositions, whether aqueous or oils, in a concentration in the range of from 2–50 mg./ml. Lower concentrations require needless quantities of liquid. Higher concentrations than 50 mg./ml. are difficult to maintain and are preferably avoided.

Oral administration forms of the drug can also be prepared for laboratory animals or human patients provided that they are encapsulated for delivery in the gut. The drug is subject to enzymatic breakdown in the acid environment of the stomach. The same dosage levels can be used as for injectable forms; however, even higher levels can be used to compensate for biodegradation in the transport. Generally, a solid unit dosage form can be prepared containing from 0.5 mg. to 25 mg. active ingredient.

Whatever the mode of administration, doses in the range of about 0.10 to 20 milligrams per kilogram, preferably 1–10 mg./kg./day, of body weight administered one to four times per day are used, the exact dose depending on the age, weight, and condition of the patient, and the frequency and route of administration.

The low cost and ready accessibility of the compounds of this invention make them particularly promising for applications in veterinary medicine, in which field their utilities are comparable to those in human medicine.

SYNTHETIC METHODS

A. General Synthesis

The novel compounds which are obtained by the primary synthetic procedures employed in this invention are those of formula I in which R is carboxy. These compounds may thus be represented by the following formula:

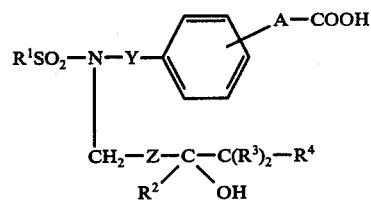

wherein A, Y, $R^1$, Z, $R^2$, $R^3$, and $R^4$ are as defined for formula I.

The general synthetic method consists of three steps.

1. A lower alkyl sulfonamide, $R^1SO_2NH_2$ is converted to its anion, $R^1SO_2NH^-$, by treatment with a strong base, preferably sodium hydride, in a suitable aprotic solvent or solvent mixture such as dimethylformamide, glyme, diglyme, or dimethylformamide-benzene. Conversion of the sulfonamide to its anion usually requires heating with tempeatures in the range 50°–95° C. being particularly advantageous. The anion is then treated with an alkylating agent of formula III:

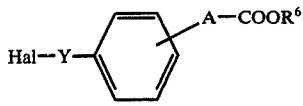

wherein $R^6$ is lower straight-chain alkyl, preferably ethyl or methyl, Hal is chlorine, bromine, or iodine, and A and Y are as defined previously. The displacement reaction of anion will III generally requires heating at 60°-90° C. for periods of 4 to 20 hours. The product obtained from this reaction can be represented by formula IV:

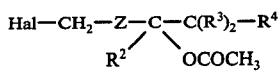

2. Alkylated sulfonate IV is then converted to its anion by treatment with a strong base, preferably sodium hydride in solvents and at temperatures as described for the similar operation in step one. The anion in solution is treated with an alkylating agent of formula V:

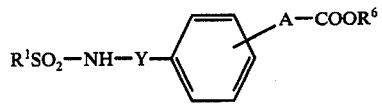

wherein Hal is chlorine, bromine, or iodine, and Z, $R^2$, $R^3$, and $R^4$ are as defined previously. This reaction generally requires heating at 80°-100° C. for periods of 8-30 hours. The product obtained can be represented by formula VI:

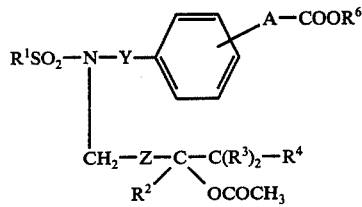

It should be noted tha the order of alkylation is immaterial. Thus, VI may be obtained by alkylating $R^1SO_2NH_2$ first with V and then with III.

3. The third step is the hydrolysis of the protecting ester functions of intermediates VI to give the hydroxy acid products of the invention having formula II. This hydrolysis can be carried out under acidic conditions (acetic acid - dilute hydrochloric acid) but the preferred conditions for hydrolysis consist of dissolving intermediates VI in a mixture of 5-10% aqueous sodium hydroxide and methanol or ethanol and allowing the hydrolysis to proceed at 25°-60° C. for a period of 4-24 hours.

B. Derivatization of Products of Formula II

1. When the groups A or Z in alkylating agents III and V are unsaturated (i.e., contain double or triple bonds), the products II derived from them will be unsaturated; i.e., they will have one or more double or triple bonds in groups A and Z. Such products can be hydrogenated over platinum or palladium catalysts to yield further saturated products of this invention of formula II wherein A and Z are ethylene.

2. To obtain carboxy salts, the acids II are dissolved in a solvent such as ethanol, methanol, glyme, and the like, and the solution treated with an appropriate alkali or alkaline earth hydroxide or alkoxide to yield the metal salt, or with an equivalent quanitity of ammonia, amine, or quaternary ammonium hydroxide to yield the amine salt. In each instance, the salt either separates from the solution or may be recovered by evaporation of the solvent. Aqueous solutions of the salts can be prepared by treating an aqueous suspension of II with an equivalent amount of an alkali metal or alkaline earth hydroxide or ammonia, an amine, or a quaternary ammonium hydroxide.

3. To obtain carboxy esters (i.e., compounds of formula I where R is $COOR^5$), the acid products II preferably are treated in ether with an ethereal solution of the appropriate diazoalkane. For example, methyl esters are produced by the reaction of II with diazomethane.

C. Preparation of Reagents

1. The reagents III which have the following general formula:

wherein Hal, $R^6$, A, and Y are as described previously, are a broad group of compounds, some of which have been described in the chemical literature. No single general method of synthesis can be prescribed for the remainder of these compounds; a variety of known organic reactions can be selected for their preparation, depending on the length and nature of the chains A and Y and the orientation of these chains on the benzene ring (ortho, meta, or para). The following examples are chosen to illustrate the procedures that are most useful in the preparation of the reagents III.

a. Reagents III with Para Orientation (1) When Hal is Br, $R^6$ is ethyl, A is $(CH_2)_o$ (a single bond), Y is $(CH_2)_3$, and A and Y are in the para orientation, reagent III becomes ethyl 4-(3-bromopropyl)-benzoate (VII):

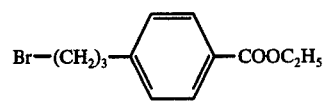

To prepare VII, 3-bromopropylbenzene is acylated with acetyl chloride in the presence of aluminum chloride; the resulting acetophenone is oxidized with sodium hypobromite to 4-(3-bromopropyl)benzoic acid, and the acid is esterified with ethanol and mineral acid catalyst to afford VII.

(2) When Hal is Cl, $R^6$ is ethyl, A is oxymethylene, Y is $CH_2$, and A and Y are para, reagent III becomes ethyl 4-chloromethylphenoxyacetate (VIII):

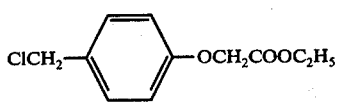

VIII

Reagent VIII is prepared by the chloromethylation of ethyl phenoxyacetate, which procedure consists of heating ethyl phenoxyacetate with formaldehyde and concentrated hydrochoric acid.

b. Reagents III with Meta Orientation (1) When Hal is Br, $R^6$ is ethyl, A is $(CH_2)_2$, Y is $CH_2$, and A and Y are meta, reagent III becomes ethyl m-bromomethylhydrocinnamate (IX):

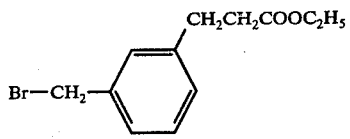

IX

Since reagent IX is difficult to prepare, it is advantageous to use its functional equivalent, the reagent X, shown below. Alkylation of an alkanesulfonamide with X gives a product XI which can be hydrogenated to give the same intermediate XII which would be obtained on alkylation of the sulfonamide with IX.

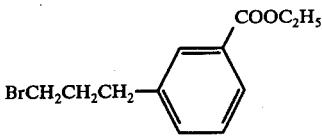

XIII

Compound XIII is prepared by the following series of reactions: (1) ethyl m-toluate is brominated with N-bromosuccinimide in $CCl_4$ to give ethyl 3-bromomethylbenzoate; (2) the bromo compound is treated with sodio bis-tert-butyl malonate and the product heated in toluene with a catalystic amount of a strong acid (preferably p-toluene-sulfonic acid) to effect elimination and decarboxylation and afford m-ethoxycarbonylhydrocinnamic acid; (3) the latter compound is made to react with thionyl chloride and the resulting acid chloride is reduced with potassium or sodium borohydride to yield ethyl 3-(3-hydroxypropyl)-benzoate; (4) the hydroxy ester is treated with phosphorus tribromide is ether to give reagent XIII.

c. Reagents III with Ortho Orientation

When Hal is Br, $R^6$ is ethyl, A is $(CH_2)_o$, Y is $(CH_2)_4$, and A and Y are ortho, reagent III becomes ethyl 2-(4-bromobutyl)benzoate (XIV):

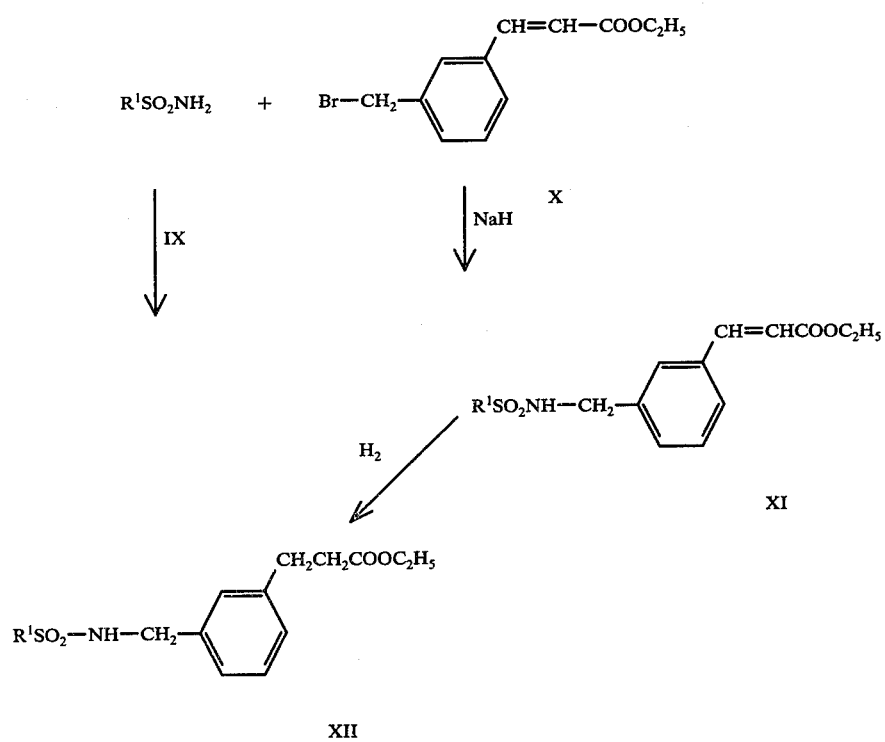

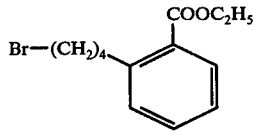

XIV

Reagent X (ethyl m-bromomethylcinnamate) is prepared by the reaction of N-bromosuccinimide with ethyl m-methylcinnamate in carbon tetrachloride solution.

(2) When Hal is Br, A is $(CH_2)_o$, $R^6$ is ethyl, Y is $(CH_2)_3$, and A and Y are meta, reagent III becomes ethyl 3-(3-bromopropyl)benzoate (XIII):

Compound XIV is prepared by the following series of reactions. (1) o-Toluic acid is converted to its dianion with lithium diisopropylamide; (2) the dianion is treated with 4-(tetrahydropyranyloxy)butyl bromide and the crude alkylate is heated with ethanol and a catalytic amount of mineral acid to yield ethyl 2-(4-hydroxybutyl)-benzoate; (3) the hydroxy ester in ether is treated with phosphorus tribromide to yield reagent XIV.

2. The reagents V which have the following general formula:

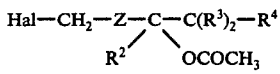    V wherein Hal, Z, $R^2$, $R^3$, and $R^4$ are as described previously, are prepared by processes that are selected principally on the basis of the nature of group Z.

a. When Z is ethylene, the reagents V can be represented by the general formula XV:

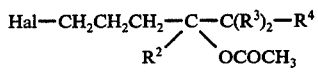    XV (1) In a general process that is useful when $R^2$ is hydrogen, a Grignard reagents

is allowed to react in ether or tetrahydrofuran with a 4-halobutyronitrile, $$Hal-CH_2CH_2CH_2CN.$$

The immediately resulting imine is hydrolyzed in aqueous acidic solution to give ketones of the formula

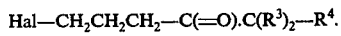

The ketones are reduced to the alcohols

with sodium or potassium borohydride in a suitable solvent such as methanol, ethanol, or diglyme. Acetylation of these alcohols, preferably with acetic anhydride, gives the reagents XV where $R^2$ is H.

(2) A variant of the first process that is particularly useful when both $R^3$ groups are methyl and $R^2$ is hydrogen consists in reacting Grignard reagents $$R^4-C(CH_3)_2-MgCl$$

with 4-halobutyryl chlorides, $$Hal-CH_2CH_2CH_2COCl.$$

The resulting ketones,

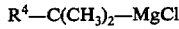

are reduced to the alcohols and acetylated as above to give the reagents XV wherein $R^3$ is methyl and $R^2$ is H.

(3) A process useful in preparing reagents XV where $R^2$ is methyl consists in reacting Grignard reagents

with halo ketones $$Hal-CH_2CH_2CH_2COCH_3$$

and treating the resulting Grignard complex with acetic anhydride to yield reagents XV where $R^2$ is methyl. b. When Z s vinylene, the reagents V can be represented by the general formula XVI:

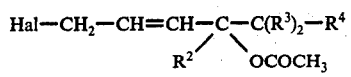    XVI

A particular useful method for the preparation of reagents XVI consists in treating an $\alpha,\beta$-unsaturated carbonyl compound $$CH_3CH=CH-C(=O)-R^2$$

with Grignard reagents

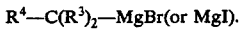

The products of this reaction obtained after the usual workup are

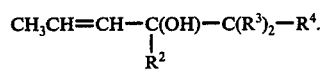

These alcohols are acetylated, preferably with acetic anhydride, to give the acetoxy intermediates

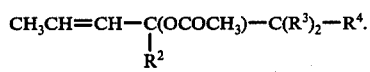

These intermediates are allowed to react with N-bromo-succinimide in carbon tetrachloride at 50°–70° C. to 5 hours to effect allylic bromination and give the reagents XVI.

c. When Z is ethynylene, the reagents V can be represented by the general formula XVII:

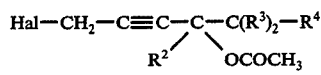    XVII

Reagents XVII are prepared by a process that is of further advantage in that it can be used for the preparation of those compounds where $R^4$ and $R^2$ (methyl) are joined together to form carbocyclic rings. The starting materials for the process are aldehydes or ketones with the structure $$R^2-C(=O)-C(R^3)_2-R^4.$$

Examples of such aldehydes and ketones are hexanal, 2-methylhexanal, 2-heptanone, and (when $R^4$ is joined either with $R^2$ when $R^2$ is methyl or with the carbon bearing $R^2$ is hydrogen as earlier specified) cyclohexanone or cyclooctanone. Such alehydes or ketones are caused to react with lithium acetylide or ethynylmagnesium bromide to give alcohols of the structure

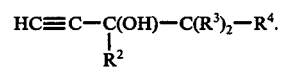

These alcohols are acetylated preferably with acetic anhydride in pyridine solution. The resulting acetates are heated with formaldehyde (preferably introduced in the form of paraformaldehyde) and dimethylamine or diethylamine to give amines

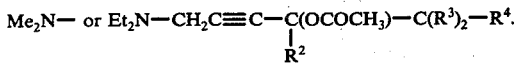

The amines are caused to react with cyanogen bromide, preferably in ether solution at 25°—35° C. and from 8 to 24 hours to give the reagents XVII.

This process is also of particular advantage in peparing alkylating agents XVII used for the synthesis of the compounds of formula II wherein the chiral carbon atom bearing $R^2$ and OH is exclusively in ether the R or the S configuration. Such alkylating agents can be represented by the formula XVII-A:

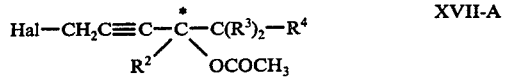
XVII-A where the asterisk denotes a carbon atom that is "resolved"; i.e., that is exclusively in either the R or S configuration.

In the synthesis of XVII-A, the above mentioned alcohols.

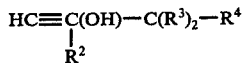

must be resolved into their constituent R and S enantiomers. The methods used for resolution are described fully by A. W. Ingersoll IN ORGANIC REACTIONS, Vol. II, R. Adams Ed., John Wiley and Sons, Inc., New York, N.Y., 1944, p. 376. The enantiomeric alcohols, once in hand, are carried forward to intermediates XVII-A exactly as described previously.

EXAMPLE 1

Preparation of 4-{3-[N-(4-Hydroxynonyl)methanesulfonamido]-propyl}benzoid Acid

Step A(1): Preparation of p-(3-Bromopropyl)acetophenone

A suspension of aluminum chloride (84 g.,; 0.63 mole) in a mixture of acetyl chloride (45 ml.) and carbon disulfide (300 ml.), under nitrogen, is cooled in an ice bath and treated, dropwise, over a 30 minute period, with a mixture of 3-phenylpropyl bromide (119.5 g., 0.60 mole) and acetyl chloride (93 ml.). At the end of the addition, the temperature is 5°–10° C. and a brown solution is obtained. The cooling bath is removed and stirring is continued at room temperature for 2 hours.

The reaction mixture is poured into a miture of finely ground ice (600 g.) and concentrated hydrochloric acid (60 ml.). The resulting oil is extracted into ether and the combined extracts are washed well with water and then dried over anhydrous magnesium sulfate. The solvents are removed under reduced pressure, followed by a benzene chaser, to give 105.6 g. (theory 144.68 g.) of light, orange-red residual oil. This oil is distilled from a 250 ml. Claisen, without a column, to give the title compound as a light yellow oil, yield 119.6 g (83%), b.p. 185°–187° C./14mm.

Step A(2): Preparation of p-(3-Bromopropyl)benzoic Acid

A solution of sodium hydroxide (163.68 g.; 4.092 moles) in water (1400 ml.) and dioxane (1000 ml.) is chilled in a salt-ice bath to 15° C. and treated, dropwise, over 30 minutes with bromine (238.10 g., 1.488 moles) at 10–15° C. Then p-(3-bromopropyl)acetophenone (119.60 g.; 0.496 mole) is added, dropwise, over 1 hour at 5°–10° C., employed good stirring. Stirring at 0°–5° C. is continued until the hypobromite is exhausted. The time required is 2 hours.

The reaction solution is acidified with an excess of concentrated hydrochloric acid. The supernatant is decanted from a semi-solid which separates. The semi-solid is dissolved in ether and the ether solution is washed well with water and then dried over anhydrous magnesium sulfate. The ether is removed under reduced pressure to give a semi-solid residue. The residual semi-solid is stirred with petroleum ether. The resulting white solid is collected by filtration and washed with petroleum ether. The yield of the title compound is 100.8 g. (84%), m.p. 115°–118° C. (Lit. Ref.: F. F. Blicke and W. M. Lilienfeld, J. Am. Chem. Soc., 65, 228 (1943) gives m.p. 118°–120° C. after recrystallization from a mixture of benzene and petroleum ether.)

Step A(3): Preparation of Ethyl 4-(3-Bromopropyl)benzoate

A mixture of p-(3-bromopropyl)benzoic acid (100.8 g.; 0.41 mole), benzene (290 ml.), ethanol (60 ml.) and concentrated sulfuric acid (1.4 ml.) is heated under reflux under a Dean and Stark constant water separator until the evolution of water ceases. The time required is 23 hours.

The cold reaction mixture is washed with water (230 ml.), saturated sodium bicarbonate solution (115 ml.), water (230 ml.) and then dried over anhydrous magnesium sulfate. The solvents are removed under reduced pressure to give 113.4 g. (theory 111.18 g.) of light, orange-red residual oil. This oil is distilled from a 250 ml. Claisen, having a 15 cm. Vigreux column to give the title compound as a colorless oil, yield 99.0 g. (89%), b.p. 136°–139° C./0.05 mm.

Step B: Preparation of N-(4-Acetoxynonyl)methanesulfonamide

Sodium hydride (2 g., 0.083 mole) is suspended in benzene (60 ml.) and dimethylformamide (120 ml.). Methanesulfonamide (7.6 g., 0.08 mole) is added and the suspension is heated on the steam bath for two hours. After the mixture is cooled in an ice bath, 1-chloro-4-acetoxynonane (18.5 g., 0.084 mole) is added dropwise with stirring over one hour. The suspension is heated on the steam bath for twenty hours and separated between ethyl acetate and water. After being washed with water, the organic layer is dried over anhydrous magnesium sulfate. Evaporation of the ethyl acetate in vacuo and distillation through a short path column gives the title compound, 11.6 g. (52%), b.p. 182°–185° C./0.08 mm. Anal. Calcd. for $C_{12}H_{25}NO_4S$: C, 51.58; H, 9.02; N, 5.01. Found: C, 52.33; H, 8.84; N, 4.91.

Step C: Preparation of Ethyl 4-{3-[N-(4-Acetoxynonyl)-methanesulfonamide]-propyl}benzoate A suspension of sodium hydride (0.85 g.; 0.0354 mole) in a solvent mixture of benzene (16 ml.) and dimethylformamide (16 ml.) is treated, dropwise, over 15 minutes with N-(4-acetoxynonyl)methanesulfonamide (9.00 g.; 0.0322 mole). Stirring is continued for an additional 15 minutes. Then ethyl 4-(3-bromopropyl)benzoate (9.60 g.; 0.0354 mole) is added, dropwise, over 15 minutes. The mixture is heated to 90° C. over 1 hour and maintained at 90° C. for 2 hours.

The cooled reaction mixture is treated with water (65 ml.) and the organic layer is separated. The aqueous layer is extracted with ether. The combined organic solutions are washed with saturated sodium chloride solution and then dried over anhydrous magnesium sulfate. The solvents are removed under vacuum to give the title compound as a residual oil. The yield is 15.12 g.; pmr (CDCl$_3$) δ 2.02 (3H, s CH$_3$COO), 2.68 (3H, s CH$_3$SO$_2$), 3.17 (4H, superimposed triplets CH$_2$NCH$_2$), 4.33 (2H, q COOCH$_2$CH$_3$), 4.92 (1H, m HCOCOCH$_3$).

Step D: Preparation of 4-{3-[N-(4-Hydroxynonyl)methanesulfonamido]-propyl}benzoic Acid Ethyl 4-{3-[N-(4-Acetoxynonyl)methanesulfonamido]propyl}benzoate (15.12 g.; 0.0322 mole) is added to a solution of sodium hydroxide (3.86 g; 0.0966 mole) in water (18 ml.) and methanol (162 ml.). The resulting solution is heated under reflux for 2 hours.

The methanol is removed under vacuum. The residue is dissolved in water (150 ml.) and acidified with concentrated hydrochloric acid to the congo red endpoint. The resulting white solid is collected and dried. The yield of the title compound is 12.87 Sg. (100%), m.p. 74°–80° C. Recrystallization from butyl chloride gives 8.73 g. (68%) of mica-like, white crystals, m.p. 102.5°–103.5° C.; pmr (CDCl$_3$) δ 2.82 (3H, s CH$_3$SO$_2$), 3.17 (4H, superimposed triplets CH$_2$NCH$_2$), 3.63 (1H, m HCOH), 6.80 (2H, s OH and COOH). Anal. Calcd. for C$_{20}$H$_{33}$NO$_5$S: C, 60.12; H, 8.33; N, 3.50. Found: C, 60.20; H, 8.12; N, 3.47.

EXAMPLE 2

Preparation of 4-{3-[N-(4-Hydroxynonyl)ethanesulfonamido]-propyl}benzoic Acid This compound is prepared by the series of reactions described in Example 1 except that in Step B, an equivalent amount of ethanesulfonamide is substituted for the methanesulfonamide employed in Example 1. The product of Step B of the present example is thus N-(4-acetoxynonyl)-ethanesulfonamide. The product of Step C becomes ethyl 4-{3-[N-(4-acetoxynonyl)ethanesulfonamido]propyl}benzoate, and of Step D, 4-{3-[N-(4-hydroxynonyl)ethanesulfonamido]propyl}benzoic acid.

EXAMPLE 3

Preparation of 4-{3[N-(4-Hydroxy-2-nonenyl)methanesulfonamido]-propyl}benzoic Acid

Step A: Preparation of Ethyl 4-(3-Methanesulfonamidopropyl)benzoate

A suspension of sodium hydride (1.76 g.; 0.0735 mole) in a solvent mixture of benzene (50 ml.) and dimethylformamide (50 ml.) is treated, in one portion, with methanesulfonamide (6.66 g; 0.070 mole). The mixture is heated at 90° C. for 2 ½ hours, cooled to 25° C., and treated with ethyl 4-(3-bromopropyl)benzoate (19.04 g.; 0.070 mole) in one portion. The mixture is then heated at 90° C. for 28 hours with good stirring.

The cooled reaction mixture is treated with water (200 ml.), and the organic layer is separated. The aqueous layer is extracted with ether. The combined organic solutions are washed with saturated sodium chloride solution and then dried over anhydrous magnesium sulfate. The solvents are removed under vacuum to give 19.24 g. of an orange residual oil. The oil is purified by column chromatography on silica gel with 2% methanol in chloroform as eluant. A light yellow oily forerunner, 4.70 g., showing a single spot, Rf=0.56, on thin layer chromatography on silica gel with 2% methanol in chloroform as eluant, is indicated to be the bisalkylated by-product. The title compound is obtained as a light yellow oil, 6.97 g., showing a single spot, Rf=0.30, on thin layer chromatography on silica gel with 2% methanol in chloroform as eluant, pmr (CDCl$_3$) δ 1.38 (3H, t COOCH$_2$CH$_3$), 1.97 (2H, m CH$_2$CH$_2$CH$_2$), 2.68 (2H, t CH$_2$C$_6$H$_4$), 2.93 (3H, s CH$_3$SO$_2$), 3.15 (2H, m NHCH$_2$), 4.35 (2H, q COOCH$_2$CH$_3$), 4.88 (1H, m NH), 7.22 (2H, d 3,5 phenyl H), 7.92 (2H, d 2,6 phenyl H).

Step B: Preparation of Ethyl 4-{3-[N-(4-Acetoxy-2-nonenyl)methanesulfonamido]-propyl}benzoate A suspension of sodium hydride (1.2 g., 0.05 mole) in benzene (50 ml.) and dimethylformamide (50 ml.) is treated with ethyl 4-(3-methanesulfonamidopropyl)benzoate (14.3 g., 0.05 mole). The mixture is heated at 90° C. for 2.5 hours and then cooled to 25° C. and treated with 1-bromo-4-acetoxy-2-nonene (13.2 g., 0.05 mole). The mixture is then stirred and heated at 90° C. for 8 hours.

The reaction mixture is cooled, treated with water (250 ml.), and the organic layer separated, washed with water and brine, and dried over magnesium sulfate. The solvent is removed under vacuum. The residual oil consisting of the crude title compound is chromatographed on a column containing 350 g. of silica gel with elution by a 2% solution of methanol in chloroform. The title compound, purified in this manner, is obtained as a yellowish, viscous oil.

Step C: Preparation of 4-{3-[N-(4-Hydroxy-2-nonenyl)-methanesulfonamido]-propyl}benzoic Acid Ethyl 4-{3-[N-(4-Acetoxy-2-nonenyl)methanesulfonamido]propyl}benzoate (23.4 g., 0.05 mole) is added to a solution of sodium hydroxide (6.0 g., 0.15 mole) in water (30 ml.) and methanol (300 ml.). The resulting solution is boiled under reflux for 2 hours.

The methanol is removed by distillation at reduced pressure. The residue is dissolved in water (300 ml.) and the solution acidified with concentrated hydrochloric acid. The title compound precipitates from solution and is purified by recrystallization.

EXAMPLE 4

Preparation of 4-{3-[N-(3-(1-Hydroxycyclohexyl)-2-propynyl)methanesulfonamido]propyl}benzoic Acid This compound is prepared by the series of reactions described in Example 3 except that in Step B, an equivalent amount of 1-(3-bromo-1-propynyl)-1-acetoxycyclohexane is substituted for 1-bromo-4-acetoxy-2-nonene and the heating period at 90° C, is shortened to 4 hours. There is thus obtained in Step B of this example, ethyl 4-{3-[N-(3-(1-acetoxycyclohexyl)-2-propynyl)methanesulfonamido]propyl}benzoate. Saponification of this ester in Step C yields 4-{3-[N-3-(1-hydroxycyclohexyl)-2-propynyl)-methanesulfonamido]propyl}benzoic acid.

EXAMPLE 5

Preparation of
4-{3-]N-(3-(1-Hydroxycyclohexyl)propyl)-methanesulfonamido]propyl}benozic Acid 4-{3-[N-(3-(1-Hydroxycyclohexyl)-2-propynyl)-methanesulfonamido]propyl}benozic acid (3.9 g., 0.01 mole) in ethyl acetate (50 ml.) is hydrogenated over 2.0 g. of a 5% Pt on charcoal catalyst at 1 atmosphere of pressure and room temperature. When the theoretical amount of hydrogen (0.02 mole) is absorbed, the catalyst is filtered off and the solvent evaporated to afford the title compound.

EXAMPLE 6

Preparation of
4-{3-[N-(4-Hydroxy-4-methylnonyl)methanesulfonamido]propyl}benzoic Acid

Step A: Preparation of 1-Chloro-4-acetoxy-4-methylnonane

To the Grignard reagent prepared from 1-bromopentane (4.8 g., 0.04 mole) and magnesium (0.96 g., 0.04 mole) in ether is added 5-chloro-2-pentanone (6.0 g., 0.04 mole). The reaction mixture is stirred at 25° C. for 1 hour and then cooled to 15° C. Acetic anhydride (6 ml., excess) is added carefully and the solution is allowed to stand for 20 hours. Water is added, and the ether layer is separated, washed with brine, and dried over sodium sulfate. Distillation affords the title compound in 4.3 g. (46%) yield, b.p. 88° C. (0.1 mm.). Anal. Calcd. for $C_{12}H_{23}ClO_2$: C, 61.39; H, 9.87. Found: C, 60.99; H, 10.19.

Step B: Preparation of Ethyl 4-{3-[N-(4-Acetoxy-4-methylnonyl)methanesulfonamido]propyl}benzoate This compound is prepared by the method described in Example 3, Step B, except that an equivalent quantity of 1-chloro-4-acetoxy-4-methylnonane is substituted for 1-bromo-4-acetoxy-2-nonene and the heating period at 90° C. is extended to 28 hours.

Step C: Preparation of 4-{3-[N-(4-Hydroxy-4-methylnonyl)-methanesulfonamido]propyl}benzoic Acid This compound is prepared by the method described in Example 3, Step C, except that the ester product of Step B of the present example is substituted in equivalent amount for the ethyl 4-{3-[N-(4-acetoxy-2-nonenyl)methanesulfonamido]propyl}benzoate employed in Example 3, Step C.

EXAMPLE 7

Preparation of
4-{3-[N-(4-Hydroxyundecyl)methanesulfonamido]propyl}benzoic Acid

This compound is prepared by the series of reactions described in Example 3, except that in Step B an equivalent amount of 1-chloro-4-acetoxyundecane is substituted for 1-bromo-4-acetoxy-2-nonene and the heating period at 90° C. is extended to 28 hours. There is thus obtained in Step B of this example, ethyl 4-{3-[N-(4-acetoxyundecyl)methanesulfonamido]propyl}benzoate. Saponficiation of this ester in Step C yields 4-{3-[N-(4-hydroxyundecyl)methanesulfonamido]propyl}benzoic acid.

EXAMPLE 8

Preparation of
4-{3-[N-(4-Hydroxy-8-nonenyl)methanesulfonamido]propyl}benozic Acid

Step A(1): Preparation of 1-Chloro-8-nonen-4-one

To the Grignard reagent prepared from a mixture of 5-bromopentene-1 (100.00 g.; 0.671 mole) and magnesium (16.32 g.; 0.671 mole) in ether (450 ml.) is added, dropwise, during 1 hour, 4-chlorobutyronitrile (69.49 g.; 0.671 mole). Stirring is continued for an additional 1 hour.

The reaction mixture is poured into a mixture of finely crushed ice (470 g.) and concentrated hydrochloric acid (335 ml.). The ether layer is separated quickly and discarded. The aqueous layer is heated on a steam bath for 1 hour to hydrolyze the intermediate imine and cause the separation of the ketone as an oil. After cooling, the oil is extracted with ether and the combined extracts are washed with saturated sodium chloride solution and dried over anhydrous magnesium sulfate. The solvent is removed under vacuum and the residual oil is distilled to give the title compound as a light yellow oil, yield 23.7 g. (14%), b.p. 108°–112° C./16mm.

Step A(2): Preparation of 1-Chloro-8-nonen-4-ol

A suspension of sodium borohydride (2.55 g.; 0.0675 mole) and sodium hydroxide (0.51 g.) in ethanol (122 ml.) is treated, dropwise, over 1 hour with 1-chloro-8-nonen-4-one (23.6 g.; 0.135 mole) while the temperature is maintained at 45°–50° C. Stirring is continued for 1 hour longer without external cooling.

The reaction mixture is acidified with concentrated hydrochloric acid to the Congo red endpoint and then the ethanol is removed under vacuum. The residue is treated with water (80 ml.) and the resulting oil is extracted with ether. The combined extracts are washed with saturated sodium chloride solution and dried over anhydrous magnesium sulfate. The solvent is removed under vacuum to give the title compound as a yellow residual oil, yield 22.10 g. This oil is used in the next step without purification.

Step A(3): Preparation of 1-Chloro-4-acetoxy-8-nonene

A mixture of 1-chloro-8-nonen-4-ol (22.10 g.; 0.125 mole) and acetic anhydride (25.52 g.; 0.0250 mole) is heated on a steam bath for 1 ½ hours.

The volatile materials are removed under vacuum and the residua oil is distilled to give the title compound as a colorless oil, yield 14.03 g. (51%), b.p. 134°–136° C.16mm.; pmr (CDCl$_3$ δ 2.07 (3H, s CH$_3$COO), 3,53 (2H, t CH$_2$Cl), 4.78–5.23 (2H, m CH=CH$_2$), 5.28–6.18 (1H, m CH=CH$_2$).

Step B: Preparation of Ethyl 4-{3-[N-(4-Acetoxy-8-nonenyl)methanesulfonamido]propyl}benzoate This compound is prepared by the method described in Example 3, Step B, except that an equivalent quantity of 1-chloro-4-acetoxy-8-nonene is substituted for 1-bromo-4-acetoxy-2-nonene and the heating period at 90° C. is extended to 28 hours.

Step C: Preparation of 4-{3-[N-(4-Hydroxy-8-nonenyl)-methanesulfonamido]-propyl}benzoic Acid This compound is prepared by the method described in Example 3, Step C, except that the ester product of Step B of the present example is substituted in equivalent amount for the ethyl 4-{3-[N-(4-acetoxy-2-nonenyl)methanesulfonamido]propyl}benzoate employed in Example 3, Step C.

EXAMPLE 9

Preparation of 4-{3-[N-(5,5-Dimethyl-4-hydroxynonyl)methanesulfonamido]propyl}benzoic Acid

Step A(1): Preparation of 1-Chloro-5,5-dimethyl-4-nonanone

Four hundred ml. of a solution in ether of 1,1-dimethylpentylmagnesium chloride prepared from mangesium (24.3 g., 1.0 mole) and 1-chloro-1,1-dimethylpentane (134.5 g., 1.0 mole) according to the procedure of Whitmore and Badertscher [J. AM. CHEM. SOC., 55, 1559 (1933)] is added dropwise with stirring to 4-chlorobutyryl chloride (197.4 g., 1.4 moles) in ether (400 ml.) during 6 hours. The reaction mixture is stirred for an additional 12 hours. It is then poured into a mixture of ice and dilute hydrochloric acid. The ether layer is separated, washed with water, and dried over sodium sulfate. The ether is evaporated and the residue distilled at aspirator vacuum through a Vigreaux column to yield the product as a colorless oil.

Step A(2): Preparation of 1-Chloro-5,5-dimethyl-4-nonanol

By following the procedure described for 1-chloro-8-nonen-4-ol (Example 8, Step A(2)) but substituting 1-chloro-5,5-dimethyl-4-nonanone for 1-chloro-8-nonen-4-one and continuing stirring and heating at 50° C. for 6 hours, there is obtained 1-chloro-5,5-dimethyl-4-nonanol.

Step A(3): Preparation of 1-Chloro-4-acetoxy-5,5-dimethylnonane

By following the procedure described for 1-chloro-4-acetoxy-8-nonene (Example 8, Step A(3)) but substituting 1-chloro-5,5-dimethyl-4-nonanol for 1-chloro-8nonen-4-ol and continuing the steam both heating for 4 hours, there is obtained, 1-chloro-4-acetoxy-5,5-dimethylnonane.

Step B: Preparation of Ethyl 4-{3-[N-(5,5-Dimethyl-4-acetoxynonyl)methanesulfonamido]propyl}benzoate This compound is prepared by the method described in Example 3, Step B, except that an equivalent quantity of 1-chloro-4-acetoxy-5,5-dimethylnonane is substituted for 1-bromo-4-acetoxy-2-nonene and the heating period at 90° C. is extended to 28 hours.

Step C: Preparation of 4-{3-[N-(5,5-Dimethyl-4-hydroxynonyl)methanesulfonamido]propyl}benzoic Acid This compound is prepared by the method described in Example 3, Step C, except that the ester product of STep B of the present example is substituted in equivalent amount for the ethyl 4-{3-[N-(4-acetoxy-2-nonenyl)methanesulfonamido]propyl}benzoate employed in Example 3, Step C.

EXAMPLE 10

Preparation of 4-{3-[N-(8,8-Dimethyl-4-hydroxynonyl)-methanesulfonamido]propyl}benzoic Acid

Step A: Preparation of 1-Chloro-4-acetoxy-8,8-dimethylnonane

This compound is prepared by the methods described in Example 8, Steps A(1), A(2), and A(3), except that in Step A(1), an equivalent quantity of 1-bromo-4,4-dimethylpentane is substituted for 5-bromopentene-1. The product of Step A(1) thus becomes 1-chloro-8,8-dimethyl-4-nonanone. Subsequent reactions yield 1-chloro-8,8-dimethylnonan-4-ol and 1-chloro-4-acetoxy-8,8-dimethylnonane.

Step B: Preparation of Ethyl 4-{3-[N-(8,8-Dimethyl-4-acetoxynonyl)methanesulfonamido]propyl}benzoate This compound is prepared by the method described in Example 3, Step B, except that an equivalent quantity of 1-chloro-4-acetoxy-8,8-dimethylnonane is substituted for 1-bromo-4-acetoxy-2-nonene and the heating period at 90° C. is extended to 28 hours.

Step C: Preparation of 4-{3-[N-(8,8-Dimethyl-4-hydroxynonyl)methanesulfonamido]propyl{benzoic Acid This compound is prepared by the method described in Example 3, Step C, except that the ester product of Step B of the present example is substituted in equivalent amount for the ethyl 4-{3-[N4-acetoxy-2-nonenyl)-methanesulfonamido]propyl}benzoate employed in Example 3, Step C.

EXAMPLE 11

Preparation of m-[N-(4-Hydroxynonyl)methanesulfonamidomethyl]-cinnamic Acid

Step A: Preparation of Ethyl m-[N-(4-Acetoxynonyl)methanesulfonamidomethyl]-cinnamate Sodium hydride (0.59 g., 0.025 mole) is suspended in benzene (20 ml.) and dimethylformamide (35 ml.). N-(4-acetoxynonyl)methanesulfonamide [Example 1, Step B] (6.1 g., 0.022 mole) is added and stirred 1 hour at room temperature. Ethyl m-bromomethylcinnamate (6.68 g., 0.025 mole) is added dropwise with stirring over 1 hour. The suspension is stirred at room temperature for 20 hours and then separated between ethyl acetate and water. After being washed with water, the organic layer is dried over anhydrous magnesium sulfate. Removal of the ethyl acetate by evaporation in vacuo gives an oil which, after chromatograpy on silica gel, gives ethyl m-[N-(4-acetoxynonyl)-methanesulfonamidomethyl]cinnamate, 4.1 g. (40% yield). Anal. Calcd. for $C_{24}H_{37}NO_6S$: C, 61.64; H, 7.98; N, 3.00 Found: C, 61.36; H, 8.40; N, 3.07

Step B: Preparation of m-[N-(4-Hydroxynonyl)methanesulfonamidomethyl]-cinnamic Acid A solution composed of ethyl m-[N-(4-acetoxynonyl)methanesulfonamidomethyl]cinnamate (4.1 g., 0.0088 mole), sodium hydroxide (1.05 g., 0.026 mole), water (15 ml.), and ethanol (75 ml.) is kept at room temperature 20 hours. The reaction mixture is added to water, extracted with ether, and the aqueous layer acidified. After extraction with ethyl acetate and drying overanhydrous magnesium sulfate, the ethyl acetate is removed by evaporation in vacuo. This gives, after crystallization from 1-chlorobutane, m-[N-(4-hydroxynonyl)methanesulfonamidomethyl]cinnamic acid, 2.6 g. (74% yield), m.p. 105° C. Anal. Calcd. for $C_{20}H_{31}NO_5S$: C, 60.42; H, 7.86; N, 3.52 Found: C, 60.69; H, 8.43; N, 3.51

EXAMPLE 12

Preparation of m-[N-(4-Hydroxynonyl)methanesulfonamidomethyl]-hydrocinnamic Acid m-[N-(4-Hydroxynonyl)methanesulfonamidomethyl]-cinnamic acid (3.0 g., 0.075 mole) dissolved in ethanol (80 ml.) is hydrogenated over 0.8 g. of a 5% Pd on charcoal catalyst at one atmosphere of pressure and room temperature. After the theoretical amount of hydrogen is absorbed, the catalyst is removed by filtration. The ethanol is evaporated and the residual solid is purified by crystallization to afford the pure title compound.

EXAMPLE 13

Preparation 2-{4-[N-(4-Hydroxynonyl)methanesulfonamido]-butyl}benzoic Acid

Step A(1): Preparation of Tetrahydro-2-(3-bromopropoxy)-2H-pyran

A solution of p-toluenesulfonic acid monohydrate (172 mg.) in dihydropyran (74.90 g., 0.890 mole) is treated dropwise over 30 minutes with 3-bromo-1-propanol (103.20 g., 0.742 mole) while the temperature is allowed to rise to 65° C. and employing external cooling when necessary to prevent further increase in temperature. Stirring is continued for an additional 15 minutes.

The reaction solution is cooled to room temperature, diluted with ether, and shaken with 5% potassium hydroxide solution (60ml.). The organic layer is separated, washed with brine, and dried over anhydrous potassium carbonate. The solvent is removed under vacuum and the residual oil is distilled to give the title compound as a colorless oil, yield 128.6 g. (78%), b.p. 89°–95° C./15mm.

Step A(2): Preparation of 2-[4-(Tetrahydro-2H-2-pyranyloxy)butyl]benzoic Acid A solution of lithium diisopropamide, prepared at 0° C. by treating a solution of diisopropylamine (58.29 g., 0.576 mole) in tetrahydrofuran (700 ml.) and hexamethylphosphoramide (72 ml.) with butyllithium (252 ml. of 2.29M solution in hexane; 0.576 mole), is treated with a solution of o-toluic acid (39.21 g., 0.288 mole) in tetrahydrofuran (230 ml.), dropwise, over 30 minutes at 0°–5° C. Stirring is continued for 30 minutes at 0° C. Then a solution of tetrahydro-2-(3-bromopropoxy)-2H-pyran (64.30 g., 0.288 mole) in tetrahydrofuran (70 ml.) is added, dropwise, over 30 minutes at 0°–5° C. The cooling bath is removed and stirring is continued for 30 minutes.

The clear reaction solution is poured into water (3000 ml.). The aqueous layer is separated and acidified with concentrated hydrochloric acid. The resulting oil is extracted with ether and the combined extracts are washed with water and then dried over anhydrous magnesium sulfate. The solvent is removed under vacuum to give the title compound as a yellow residual oil. This crude oil (65 g.) is used in the next step without purification.

Step A(3): Preparation of Ethyl 2-(4-Hydroxybutyl)benzoate

A mixture of crude 2-[4-(tetrahydro-2H-2-pranyloxy)butyl]benzoic acid (65.0 g., 0.233 mole approx.), ethanol (460 ml.) and concentrated sulfuric acid (2.6 ml.) is heated under reflux for 15 hours.

The ethanol is removed under vacuum. The residue is treated with water (400 ml.) and the resulting oil is extracted with ether. The combined extracts are washed with aqueous sodium bicarbonate solution and water and the dried over anhydrous magnesium sulfate. The solvent is removed under vacuum and the residual oil is distilled to give the title compound as a light yellow oil, yield 14.76 g., b.p. 140°–142° C./0.1mm.

Step A(4): Preparation of Ethyl 2-(4-Bromobutyl)benzoate

To a solution of ethyl 2-(4-hydroxybutyl)benzoate (41.80 g., 0.188 mole) in ether (420 ml.) is added a solution of phosphorus tribromide (18.67 g., 0.069 mole) in ether (100 ml.), dropwise over 15 minutes. Stirring is continued at room temperature for 18 hours.

The colorless reaction solution is poured into cold water (700 ml.). The organic layer is separated, washed with aqueous sodium bicarbonate solution and water, and then dried over anhydrous magnesium sulfate. The solvent is removed under vacuum and the residual oil is distilled to give the title compound as a colorless oil, yield 31.18 g. (58%), b.p. 122°–124° C./0.075mm; pmr ($CDCl_3$) δ 1.32 (3H, t $COOCH_2CH_3$), 2.95 (2H, t $CH_2C_6H_5$), 3.35 (2H, t $CH_2Br$), 4.30 (2H, q $COOCH_2CH_3$).

Step B: Preparation of Ethyl 2{4-[N-(4-Acetoxynonyl)-methanesulfonamido]butyl} benzoate This compound is prepared by the method described in Example 11, Step A, except that an equivalent amount of ethyl 2-(4-bromobutyl)benzoate is used instead of the ethyl m-bromomethylcinnamate used in Example 11, Step A.

Step C: Preparation of 2-{4-[N-(4-Hydroxnonyl)methanesulfonamideo]butyl} benzoic Acid This compound is prepared by the method described in Example 11, Step B, except that an equivalent quantity of the ester product of the Step B of the present example replaces the ethyl m-[N-(4-acetoxynonyl)methanesulfonamidomethyl]cinnamate utilized in Example 11, Step B.

EXAMPLE 14

Preparation of {4-[N-(4-Hydroxynonyl)methanesulfonamidomethyl]-phenoxy}acetic Acid This compound is prepared by the series of reactions described in Example 11, Steps A and B, except that ethyl 4-chloromethylphenoxyacetate is substituted for the ethyl m-bromomethylcinnamate used in Example 11, Step A. The product of Step A of the present example thus becomes ethyl {4-[N-(4-acetoxynonyl)methanesulfonamidomethyl]phenoxy}acetate. The product of Step B becomes {4-[N-(4-hydroxynonyl)methanesulfonamidomethyl]phenoxy}-acetic acid.

EXAMPLE 15

Preparation of Methyl 4-}3-[N-(4-Hydroxynonyl)methanesulfonamido]-propyl}benzoate A solution of diazomethane (approx. 2.5 g., 0.06 mole) in ether (150 ml.) is mixed with a solution of 4-}3-[N-(4-hydroxynonyl)methanesulfonamido]-propyl}-benzoic acid (12.0 g., 0.03 mole) in ether(100 ml.). The resulting solution is allowed to stand 4 hours at room temperature. Acetic acid is then added to destroy the excess diazomethane and the solution is washed with dilute sodium bicarbonate solution and water and dried over magnesium sulfate. Evaporation of volatile materials at reduced pressure yields the satisfactorily pure title compound.

What is claimed is:

1. The compound having the following formula:

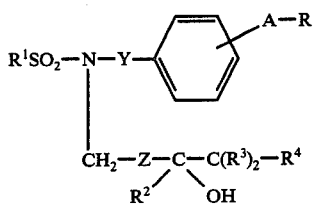

wherein

R is carboxy, a pharmaceutically acceptable carboxy salt, or alkoxycarbonyl of the formula —COOR$^5$ wherein R$^5$ is alkyl of 1-10 carbon atoms;

A is (CH$_2$)$_n$ wherein n is 0 or 2, or oxymethylene or vinylene;

Y is (CH$_2$)$_n$ wherein n is 1, 3, or 4, provided that the sum of chain-forming elements in A and Y is either 3 or 4;

R$^1$ is lower alkyl of 1-4 carbon atoms;

Z is ethylene, vinylene, or ethynylene;

R$^2$ is hydrogen or methyl;

R$^3$ is hydrogen or methyl; and

R$^4$ is lower alkyl of 3-6 carbon atoms straight or branched or 3-butenyl, provided that in one instance wherein R$^4$ is lower alkyl and R$^2$ is methyl, R$^4$ and R$^2$ are joined together with abstraction of hydrogen to form a carbocyclic ring of form 6-9 members, and further provided that in one instance when R$^4$ is lower alkyl and R$^2$ is hydrogen, R$^4$ and the carbon bearing R$^2$ and OH are joined with abstraction of hydrogen to form a carbocyclic ring of from 5-8 members.

2. The compound of claim 1 wherein R is carboxy or a carboxy salt, —COO$^-$M$^+$ wherein M$^+$ is a pharmaceutically acceptable cation derived from a metal or an amine.

3. The compound of claim 2 which has the formula:

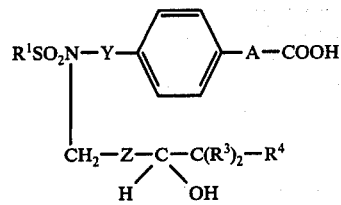

wherein

A is (CH$_2$)$_n$ wherein n is 0 or 2, or oxymethylene or vinylene;

Y is (CH$_2$)$_n$ wherein n is 1, 3, or 4;

R$^1$ is lower alkyl of 1-4 carbon atoms;

Z is ethylene, vinylene, or ethynylene;

R$^3$ is hydrogen or methyl; and

R$^4$ is lower alkyl or 3-butenyl.

4. The compound of claim 3 wherein A is (CH$_2$)$_o$, Y is (CH$_2$)$_3$, and R$^3$ is hydrogen.

5. The compound of claim 4 wherein Z is ethylene.

6. 4-{3-[N-(4-Hydroxynonyl)methanesulfonamido]-propyl}benzoic acid, the compound of claim 5 wherein R$^1$ is methyl and R$^4$ is butyl.

7. 4-{3-[N-(4-Hydroxynonyl)ethanesulfonamido]-propyl}benzoic acid, the compound of claim 5 wherein R$^1$ is ethyl and R$^4$ is butyl.

8. 4-{3-[N-(4-Hydroxyundecyl)methanesulfonamido]-propyl}benzoic acid, the compound of claim 5 wherein R$^1$ is methyl and R$^4$ is hexyl.

9. 4-{3-[N-(4-Hydroxy-8-nonenyl)methanesulfonamido]propyl}benzoic acid, the compound of claim 5 wherein R$^1$ is methyl and R$^4$ is 3-butenyl.

10. 4-{3-[N-(8,8-Dimethyl-4-hydroxynonyl)-methanesulfonamido]propyl}benzoic acid, the compound of claim 5 wherein R$^1$ is methyl and R$^4$ is 3,3-dimethylbutyl.

11. The compound of claim 4 wherein Z is vinylene.

12. 4{3-[N-(4-Hydroxy-2-nonenyl)methanesulfonamido]propyl}benzoic acid, the compound of claim 11 wherein R$^1$ is methyl and R$^4$ is butyl.

13. The compound of claim 3 wherein A is (CH$_2$)$_o$, Y is (CH$_2$)$_3$, R$^3$ is methyl, and Z is ethylene.

14. 4-{3-[N-(5,5-Dimethyl-4-hydroxynonyl)-methanesulfonamido]propyl}benzoic acid, the compound of claim 13 wherein R$^1$ is methyl and R$^4$ is butyl.

15. The compound of claim 3 wherein A is oxymethyl, Y is CH$_2$, R$^3$ is hydrogen, and Z is ethylene.

16. {4-[N-(4-Hydroxynonyl)methanesulfonamidomethyl]phenoxy}acetic acid, the compound of claim 15 wherein R$^1$ is methyl and R$^4$ is butyl.

17. The compound of claim 2 which has the formula:

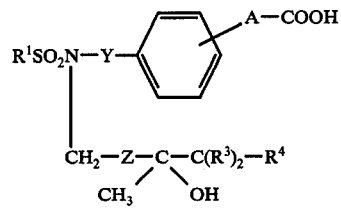

wherein

A is (CH$_2$)$_n$ wherein n is 0 or 2, or oxymethylene, or vinylene;

Y is (CH$_2$)$_n$ wherein n is 1, 3, or 4, and A and Y are in the ortho, meta, or para orientation;
R$^1$ is lower alkyl of 1–4 carbon atoms;
Z is ethylene, vinylene, or ethynylene;
R$^3$ is hydrogen or methyl; and
R$^4$ is lower alkyl or 3-butenyl.

18. 4-{3-[N-(4-Hydroxy-4-methylnonyl)methanesulfonamido]propyl}benzoic acid, the compound of claim 17 wherein A is (CH$_2$)$_o$, Y is (CH$_2$)$_3$, and A and Y are in the para orientation, R$^1$ is methyl, Z is ethylene, R$^3$ is hydrogen, and R$^4$ is butyl.

19. The compound of claim 2 which has the formula:

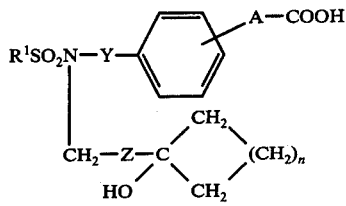

wherein
A is (CH$_2$)$_n$ wherein n is 0 or 2, or oxymethylene or vinylene;
Y is (CH$_2$)$_n$ wherein n is 1, 3, or 4, and A and Y are in the ortho, meta, or para orientation;
R$^1$ is lower alkyl or 1–4 carbon atoms;
Z is ethylene, vinylene, or ethynylene; and
n is an integer of 2 to 6.

20. 4-{3-[N-(3-(1-Hydroxycyclohexyl)-2-propynyl)methanesulfonamido]propyl}benzoic acid, the compound of claim 19 wherein A is (CH$_2$)$_o$, Y is (CH$_2$)$_3$, and A and Y are in the para orientation, R$^1$ is methyl, Z is ethynylene, and n is 3.

21. 4-{3-[N-(3-(1-Hydroxycyclohexyl)propyl)methanesulfonamido]propyl}benzoic acid, the compound of claim 19 wherein A is (CH$_2$)$_o$, Y is (CH$_2$)$_3$, and A and Y are in the para orientation, R$^1$ is methyl, Z is ethylene, and n is 3.

22. The compound of claim 2 which has the formula

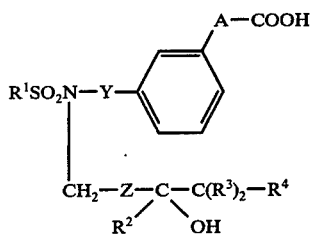

wherein
A is (CH$_2$)$_n$ wherein n is 0 or 2, or oxymethylene or vinylene;
Y is (CH$_2$)$_n$ wherein n is 1, 3, or 4;
R$^1$ is lower alkyl of 1–4 carbon atoms;
Z is ethylene, vinylene or ethynylene;
R$^2$ and R$^3$ are independently hydrogen or methyl; and
R$^4$ is lower alkyl of 3–6 carbon atoms and 3-butenyl; provided that in one instance wherein R$^4$ is lower alkyl and R$^2$ is methyl, R$^4$ and R$^2$ are joined together with abstraction of hydrogen to form a carbocyclic ring of from 6–9 members, and further provided that in one instance when R$^4$ is lower alkyl and R$^2$ is hydrogen, R$^4$ and the carbon bearing R$^2$ and OH are joined with abstraction of hydrogen to form a carbocyclic ring of from 5–8 members.

23. m-[N-(4-Hydroxynonyl)methanesulfonamidomethyl]cinnamic acid, the compound of claim 22 wherein A is vinylene, Y is CH$_2$, R$^1$ is methyl, Z is ethylene, R$^2$ and R$^3$ are hydrogen, and R$^4$ is butyl.

24. m-[N-(4-Hydroxynonyl)methanesulfonamidomethyl]hydrocinnamic acid, the compound of claim 22 wherein A is (CH$_2$)$_2$, Y is CH$_2$, R$^1$ is methyl, Z is ethylene, R$^2$ and R$^3$ are hydrogen, and R$^4$ is butyl.

25. The compound of claim 2 which has the formula:

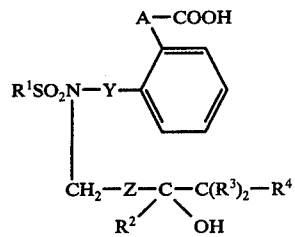

A is (CH$_2$)$_n$ wherein n is 0 or 2, or oxymethylene or vinylene;
Y is (CH$_2$)$_n$ wherein n is 1, 3, or 4;
R$^1$ is lower alkyl of 1–4 carbon atoms;
Z is etnylene, vinylene or ethynylene;
R$^2$ and R$^3$ are independently hydrogen or methyl; and
R$^4$ is lower alkyl of 3–6 carbon atoms and 3-butenyl; provided that in one instance wherein R$^4$ is lower alkyl and R$^2$ is methyl, R$^4$ and R$^2$ are joined together with abstraction of hydrogen to form a carbocyclic ring of from 6–9 members, and further provided that in one instance when R$^4$ is lower alkyl and R$^2$ is hydrogen, R$^4$ and the carbon bearing R$^2$ and OH are joined with abstraction of hydrogen to form a carbocyclic ring of from 5–8 members.

26. 2-{4-[N-(4-Hydroxynonyl)methanesulfonamido]butyl}benzoic acid, the compound of claim 25 wherein A is (CH$_2$)$_o$, Y is (CH$_2$)$_4$, R$^1$ is methyl, Z is ethylene, R$^2$ and R$^3$ are hydrogen, and R$^4$ is butyl.

27. The compound of claim 1 which has the formula:

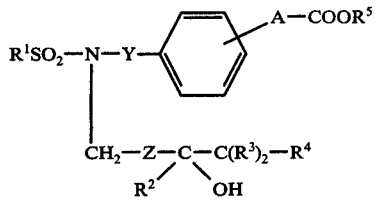

wherein
R$^5$ is alkyl of 1–10 carbon atoms;
A is (CH$_2$)$_n$ wherein n is 0 or 2, or oxymethylene or vinylene;
Y is (CH$_2$)$_n$ wherein n is 1, 3, or 4;
R$^1$ is lower alkyl of 1–4 carbon atoms;
Z is ethylene, vinylene or ethynylene;
R$^2$ and R$^3$ are independently hydrogen or methyl; and
R$^4$ is lower alkyl of 3–6 carbon atoms and 3-butenyl; provided that in one instance wherein R$^4$ is lower alkyl and R$^2$ is methyl, R$^4$ and R$^2$ are joined together with abstraction of hydrogen to form a carbocyclic ring of from 6–9 members, and further provided that in one instance when $R^4$ is lower alkyl and $R^2$ is hydrogen, $R^4$ and the carbon bearing $R^2$ and OH are joined with abstraction of hydrogen to form a carbocyclic ring of from 5–8 members.

28. Methyl 4-{3-[N-(4-Hydroxynonyl)methanesulfonamido]propyl}benzoate, the compound of claim 27 wherein $R^5$ is methyl, A is $(CH_2)_o$, Y is $(CH_2)_3$, and A and Y are in the para orientation, $R^1$ is methyl, Z is ethylene, $R^2$ and $R^3$ are hydrogen, and $R^4$ is butyl.

* * * * *